| United States Patent [19] | [11] Patent Number: 4,864,862 |
|---|---|
| Nottingham et al. | [45] Date of Patent: Sep. 12, 1989 |

[54] BORESONIC INSPECTION SYSTEM

[75] Inventors: Lawrence D. Nottingham, Charlotte, N.C.; Thomas E. Michaels; Jennifer E. Michaels, both of Freeville, N.Y.

[73] Assignee: Westinghouse Electric Corp., Pittsburgh, Pa.

[21] Appl. No.: 160,211

[22] Filed: Feb. 25, 1988

Related U.S. Application Data

[62] Division of Ser. No. 117,918, Nov. 6, 1987, Pat. No. 4,757,716.

[51] Int. Cl.$^4$ ............................................. G01N 29/04
[52] U.S. Cl. ..................................... 73/623; 73/1 DV
[58] Field of Search ............. 73/1 DV, 623, 622, 660; 367/13

[56] References Cited

U.S. PATENT DOCUMENTS 4,203,315 5/1980 Vieu et al. ......................... 73/1 DV
4,309,904 1/1982 Jones et al. ........................ 73/1 DV
4,331,021 5/1982 Lopez et al. ....................... 73/1 DV
4,567,747 12/1986 Matay ................................ 73/1 DV

*Primary Examiner*—Stewart J. Levy
*Assistant Examiner*—Robert R. Raevis
*Attorney, Agent, or Firm*—D. C. Abeles

[57] ABSTRACT

An immersion based ultrasonic inspection system is disclosed which is used to interrogate the bore and near bore material of turbine and generator rotors by passing ultrasonic search units through the rotor bore. This system utilizes variable focus array inspection transducers in a shear mode inspection of the near bore material. The flaw location method includes recording calibration transit times and transducer locations for calibration holes from which refraction angles, and material velocities are determined. When a flaw is detected the surface time for a bore surface reflection, the flaw reflection time and transducer position are used to determine the position of the flaw.

10 Claims, 7 Drawing Sheets

BORESONIC INSPECTION SYSTEM

CROSS REFERENCES TO RELATED APPLICATION

This is a Divisional application of U.S. application No. 117,918, filed Nov. 6, 1987, now U.S. Pat. No. 4,757,716. This application is related to concurrently filed U.S. applications assigned to Westinghouse and entitled ULTRASONIC SIGNAL PROCESSING SYSTEM INCLUDING A FLAW GATE by the inventors of the invention described herein and having U.S. Ser. No. 878,817 now allowed and entitled BORE MAPPING AND SURFACE TIME MEASUREMENT SYSTEM by the inventors of the invention described herein and having U.S. Ser. No. 878,649. The above-mentioned applications and patents are incorporated by reference herein. This application is also related to copending U.S. applications entitled APPARATUS FOR ULTRASONICALLY INSPECTING A LARGE SHAFT FROM A LIQUID-FILLED BORE and entitled WATER TREATMENT SYSTEM FOR ULTRASONIC INSPECTION OF TURBINE ROTORS FROM THE BORE having U.S. Pat. No. 4,699,008 and U.S. Pat. No. 4,670,029 respectively.

BACKGROUND OF THE INVENTION

The present invention is directed to an inspection system for ultrasonically inspecting a material such as metal, and, more particularly, the present invention is directed to a boresonic inspection system which performs shear mode inspection of near bore material in turbine and generator rotors by passing ultrasonic search units through an axial rotor bore and locates flaws.

In a conventional contact ultrasonic system, the emitted wave travelling through the rotor material is divergent; that is, the wave front grows in size as it moves away from the source. The intensity of this wave therefore decreases with increasing travel distance (since the area covered by the wave is increasing) and therefore, the intensity of a wave returning from a given reflector decreases with increasing distance of the reflector from the search unit Also, since most reflectors are small relative to the area (beam size) covered by the wave, the size of the reflector affects the intensity of the reflected wave. These principles have been long known and understood in ultrasonic testing in general and are used to provide an estimate of the size of an unknown reflector. The intensity of a reflected wave is normally converted, through the piezoelectric property of the transducer element, to a voltage which is then linearly presented as a signal amplitude on a cathode ray tube type presentation. Distance/Amplitude and Area/Amplitude relationships are determined using known reflectors in reference standards under conditions which reproduce or, at least, simulate the prevailing test conditions (bore curvature, attenuation, etc.). The total inspection system, including the search unit, transmit and receive electronics, amplifiers, displays, cables, etc., are calibrated using the known, artificial reflectors in a reference standard. Reflectors are considered to be reportable when their amplitudes exceed a specific amplitude limit which normally includes the Distance/Amplitude correction. Its size is estimated using the established Area/Amplitude relationship.

Some of the disadvantages associated with boresonic test systems using contact transducers are as follows:

1. Contact inspection is limited in its ability to accurately size real reflectors. Ideal reflectors, commonly flat bottom holes (with the beam normal to the flat) and side drilled holes (with the beam normal to the hole axis), are used to develop the Distance/Amplitude and Area/Amplitude relationships used for detecting and sizing reflectors with a divergent beam transducer. Since any given reflector geometry has its own reflectivity, these relationships are only valid for the type of reflector from which they were derived. Therefore, the use of a given set of relationships developed on, for example, flat bottom holes will not be accurate for other Specific geometries such as spheres, off-axis discs, elliptical notches, etc. The problem is compounded further when considering irregular, randomly oriented reflectors characteristic of real reflectors in real materials. It is for this reason that size estimates for such reflectors are normally given in terms of equivalency to the ideal reflectors used to develop the calibration relationships (such as Equivalent Flat Bottom Hole Area) and do not necessarily reflect the actual size.

2. Resolution, as used in ultrasonic testing, is defined as the ability to discriminate between two reflectors lying in close proximity to one another. Because the ultrasonic beam in a contact system is divergent, resolution is very poor. This means, for example, that a number of relatively small reflectors could be reported as one larger reflector, an error which could affect the analysis and final disposition of the rotor.

In the prior art, manual, pneumatic and motor driven inspection systems the control systems that move the scan head and provide position indications have been cumbersome and inaccurate due to resolver locations that require knowledge of mechanical slack in the system and positioning apparatus that does not allow for high resolution positioning. As a result, the location and size of discontinuities and flaws have been inaccurately located. Inaccurate flaw location, requires that remachining to remove flaws cover a larger area than is necessary, weakening the rotor at its highest stress area, near the bore. Inaccurate flaw location also hinders comparison of previous inspections with current inspections because it is difficult to determine whether a given flaw is a new flaw or an old flaw that has been inaccurately located due to alignment inaccuracies.

See U.S. Pat. No. 4,757,716 for additional discussion relating to the background of this invention.

SUMMARY OF THE INVENTION

It is a an object of the present invention to provide plural motor driven motion axes to accurately position ultrasonic transducers in a rotor for an ultrasonic inspection.

It is another object of the present invention to provide resolvers coupled to the object being moved and associated with each axis of motion to provide position information to a control computer and to the operator.

It is also an object of the present invention to provide motion axes which utilize radial displacement and rotation about a pivot to provide various combinations of surface time and refracted angle, in either a compressional or shear propagation mode.

It is yet another object of the present invention to provide a device for locating indications based on their transit times and scanner coordinates.

The present invention attains the above objects by providing an immersion based ultrasonic test system used to interrogate the bore and near bore material of turbine and generator rotors by passing ultrasonic search units through the rotor bore. This system utilizes variable focus array inspection transducers in a shear mode inspection of the bore surface and near bore material. A mapping transducer and a blind bore sensor allows the diameter of the rotor to be mapped as well as the end of a blind rotor to be detected. A carriage provides position feedback to allow accurate transducer positioning throughout the rotor. The carriage also carries a ranging transducer that allows correction of inspection beam path geometry for varying bore diameters. The control system for the plural motion axes allows accurate positioning and positioning feedback to a computer which calculates the position of discontinuities. The ultrasonic location procedure allows for flaws to be properly located in near real time during a rotor examination. The flaw location method includes recording calibration transit times and transducer locations for calibration holes from which refraction angles, and material velocities are determined. When a flaw is detected the surface time for a bore surface reflection, the flaw reflection time and transducer position are used to determine the position of the flaw.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

The present invention is a rotor ultrasonic inspection system which, based upon immersion ultrasonic test methods, utilizes variable focus shear waves generated by phased array transducers available from New York Institute of Technology. Shear waves are generally better at detecting interfaces that can be cracks in the rotor.

Figure 1:
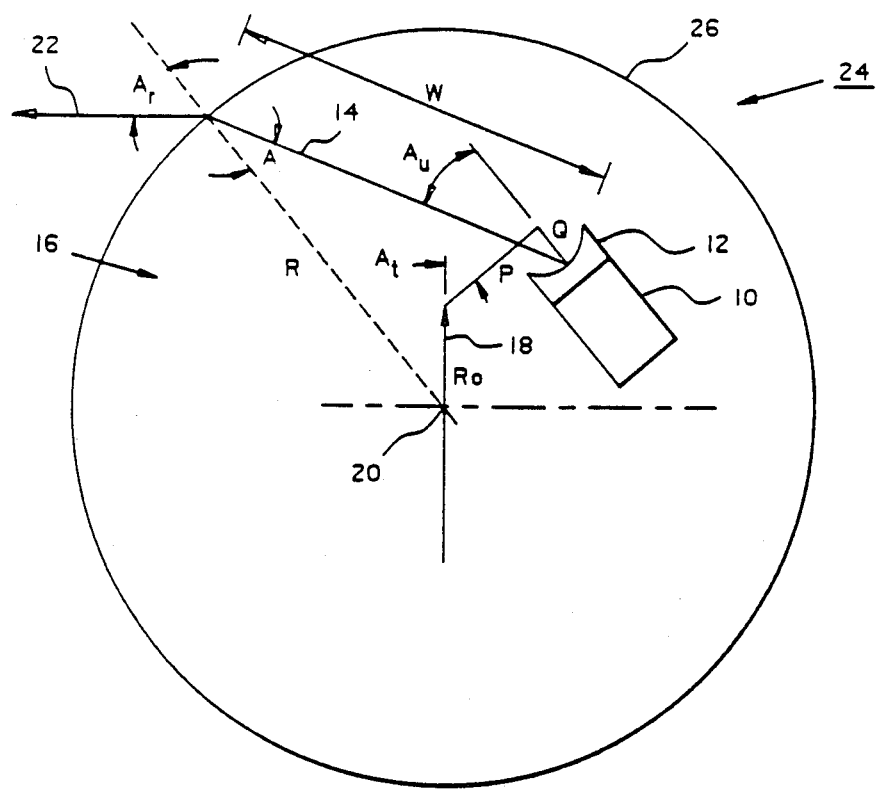
FIG. 1 depicts the relationship between an inspection transducer 10 and a rotor bore 24.

An understanding of the preferred transducer design is necessary to fully understand the present invention. Each transducer 10, as illustrated in FIG. 1, has nine elements that are concentric, planar arc segments, as in a section of an annular array (not shown). Each array transducer 10 has a lense 12 attached to the front surface such that the emitted wave 14 passes first through the lense 12 and then into an immersion fluid 16. The lense 12 is designed such that the transducer operates at a specific offset from the bore centerline 20 and when operated at this point a refracted shear beam 22 of a specific angle is generated in the rotor material 24. Beam focus is achieved through a combination of two mechanisms. First, the lense 12 causes a diffraction of the beam as it passes through the complex, concave front surface of the lense 12 into the immersion fluid 16. Second, the pulsing of the array leads to constructive and destructive interference of the sound waves generated by the various elements and to the eventual formation of a high intensity focal spot. The lense 12 corrects for the effects of the cylindrical bore curvature and creates a geometrically focused ultrasonic beam at a given depth in the rotor material 24. A geometrically focused beam is one which is focused primarily by the lense; that is, a beam that is formed by pulsing all of the elements at the same time. In this case, the geometric focal depth is approximately 1 to 1¼ inches radially below the bore surface 26 and the designed refracted angle Ar of the shear beam is approximately 40–60 degrees. The geometric focal depth and refracted angle are chosen to allow steering of the beam to the bore surface in one direction and to a depth of 4–6 inches in the other direction. Other focal depths and refracted angles are possible and in certain cases are desirable.

The beam can be steered to, and focused at, depths other than the geometric focal point by phasing the pulses applied to the various array elements in a known manner. If, for example, it is desirable to steer and focus the beam nearer the bore surface, the outer element of the transducer is pulsed first and the others pulsed sequentially from the outer elements to the inner elements. The amount of the delay provided between each of the elements controls the degree to which the beam is steered, with more delay, steering and focusing the beam nearer the surface. If the beam is to be steered and focused deeper than the geometric focal depth, the inner element is pulsed first and the sequential pulsing progresses toward the outer elements.

The steering and focusing of the beam by the phasing of the pulses applied to the various elements of the array is called transmit focus. In a real time inspection system, it is neither practical nor necessary to transmit focus on each reflector encountered. Because a given focal point has some depth of focus associated with it, a limited number of focal increments, with overlapping coverage at the transitions from one zone to the next, is sufficient. In the preferred embodiment four to six focal points providing four to six overlapping focal zones or windows is preferred when detailed inspections are necessary. In larger bores, the depth of focus is larger than in smaller bores, requiring less focal zones to get complete coverage in larger bores than in smaller bores.

A second form of focusing involves the method employed to receive the returning echoes. Receive focus is accomplished by receiving the reflected wave on more than one of the elements. For a given focal depth, specific amounts of delay are applied between the various elements receiving the returns so that the returns can be added in phase to achieve optimum signal enhancement. Continuous receive focus, as opposed to incremental receive focus, is achieved by applying appropriate delays to the return signals in hardware as a function of transit time such that the focusing is transparent to the operator. Continuous receive focusing is also referred to as dynamic focusing.

The present invention utilizes multi-element transmit focus with single element receive. This particular means of implementing the phased array technology was selected because of its capability in achieving the desired sensitivity with a minimum of system complexity. However, the present invention can utilize the above-discussed receive focus technique for higher accuracy if desired. Additional details concerning the use of the preferred transducers using the above-described methods can be obtained from the New York Institute of Technology or in the technical literature under the topic of medical ultrasonic imaging.

The present invention is an immersion system in which the bore is completely flooded with an immersion fluid and the transducers are not in contact with the bore. The present invention uses two transducers 10 to accomplish volumetric inspection, with focused beams, over the first 4-6 inches of material from the bore surface 26 radially outward. The two transducers 10 are identical and each interrogates the full volume of material described. One transducer 10 (FIG. 1) is oriented relative to the bore such that the resulting beam in the material is in a radial/circumferential plane, oriented at an angle $A_r$ of 40-60 degrees from tangent, and aiming in the clockwise direction. The second transducer 10 is identical except that its beam is aimed in the counterclockwise direction. The transducers 10 are located relative to the bore such that the incident angle $A_i$ is about 19-26 degrees and the resulting 40-60 degree refracted wave 22 in the rotor propagates in the shear mode. The outer four array elements on each side of the transducer are used as transmit elements, and the center element is used as the receiver. This configuration permits the use of a single pre-amplifier near the transducer to boost the return signals before they travel over fairly long cables to the remote electronics.

In addition to two array inspection transducers, the system contains additional single element ranging transducers located in each inspection station and used for surface tracking. These transducers are oriented such that their beams are directed radially outward with the bore surface reflection being the signal of interest. One of these ranging transducers is located in close proximity to each of the two array inspection transducers 10. They are used to track the bore surface as a function of circumferential and axial position and the measurements made with these transducers are used to correct the data collected with the array inspection transducers 10 for diameter changes, misalignment and other geometric variations. It is necessary to use separate transducers because the array transducers 10 do not receive a surface reflection when they are oriented to generate shear waves in the rotor 24. The relationship and operation of the inspection, ranging and bore mapping transducers are discussed in detail in the related applications mentioned in the cross references section.

Figure 2:
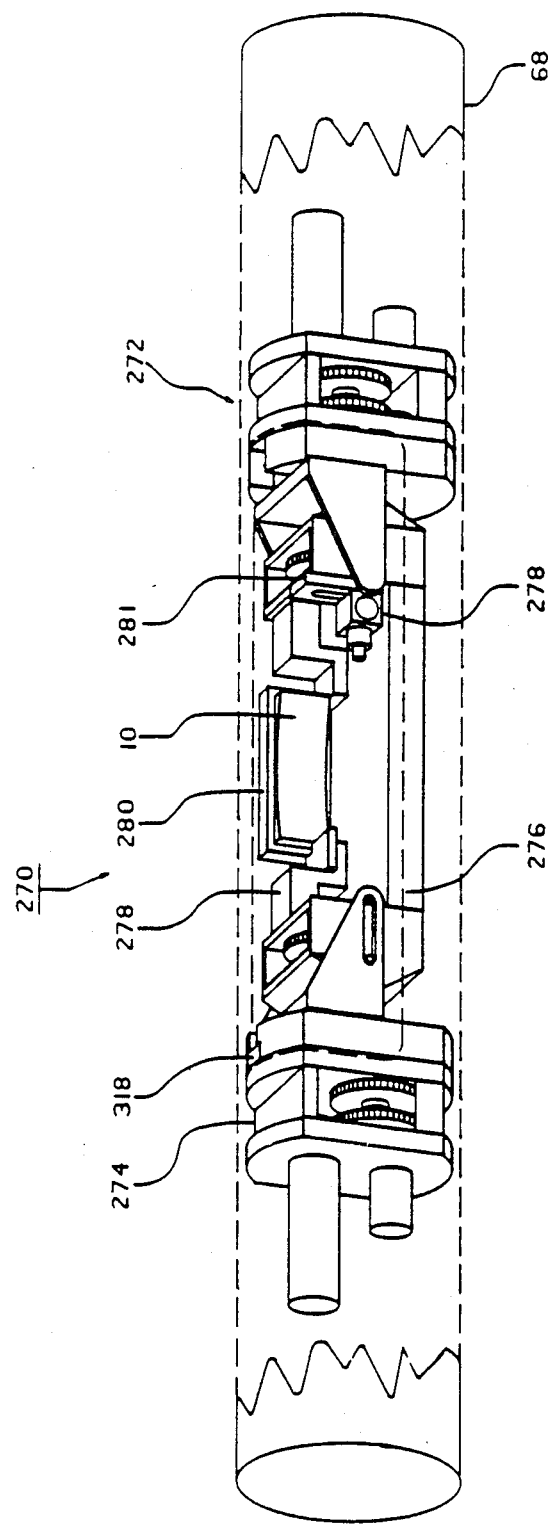
FIG. 2 is a perspective view of a carriage 270 for an inspection transducer and a ranging transducer 278 as positioned in the scan head 46.

Each of the inspection transducers 10 is mounted in a carriage which has three independent motion axes to properly position the transducer 10 such that the ultrasonic beam enters the material at the proper incident angle. Radial support assemblies 272 and 274, as illustrated in FIG. 2, provide radial adjustment of the transducer and when one radial support assembly is held at a constant level, while the other radial support assembly is moved, the transducer can be tilted. The carriage 276 attached to the radial support assemblies 272 and 274 can be used to rotate the transducer support bar 278 providing the third axis of motion. The transducer carriage also holds a ranging transducer 278 on an adjustable bracket 280.

In immersion ultrasonic testing the key parameters which must be controlled in order to maintain beam integrity are water path length, or transducer standoff distance, and incident angle, or the angle at which the beam strikes the bore surface 26. Water path length is important since reflector positions must be is determined by a calculation based on the wave transit time in combination with a knowledge of the beam path and associated travel velocities. When focused beams are used, water path length is even more significant because it affects the point within the material at which the beam will be in focus. The incident angle is important since it affects the beam propagation mode in the material (i.e., compressional mode or shear mode), its refracted angle in the material, and the intensity of the beam. All of these play key roles in maintaining inspection sensitivity, resolution, and accuracy of positional placement of reflectors. In the preferred embodiment, the transducers 10 are placed relative to the bore surface 26 such that the resultant wave in the rotor material propagates in shear mode, in a radial-circumferential plane, and at a refracted angle of about 45 degrees relative to tangent. The transducer offset and the resulting water path lengths are a matter of transducer design and can be set to any desired value.

FIG. 1 shows the key transducer position parameters for immersion based, shear mode interrogation of rotor material with the ultrasonic beam entering from the bore. The angle $A_u$ at which the ultrasonic beam exits from the transducer 10 is fixed for a particular transducer 10 by the transducer 10 and lense 12 designs. The desired refracted angle $A_r$ in the rotor material and the desired water path length W which the transducer must be offset from the bore surface 26 are determined by the transducer design. The key to achieving sensitive, accurate, repeatable inspections is to correctly position the transducer 10 relative to the bore surface so that the water path length W and the refracted angle $A_r$ are accurately set to the design values and can be repeated accurately. FIG. 1 also shows the two motion axes used in the present invention to properly position the transducer 10. The offset $R_o$ is the radial support motion and the angle $A_t$ is the transducer tilt motion. The transducer 10 offsets P and Q are setup values which are functions of the position in which the transducer 10 is mounted within the support carriage 276. During the process of mounting the transducer 10, the values for P and Q are fixed and can be measured with a mechanical measuring device, and the transducer 10 is also adjusted so that the beam is in a radial-circumferential plane, that is, the transducer 10 is adjusted so that it is not tilted axially. The values set for radial offset $R_o$ of the rotation axis and transducer tilt $A_t$ about the rotation pivot point are servo-motor driven and the positions are read by resolvers and fed back to a central computer for motion control and operator display. The water path W and refracted $A_r$ angle can be calculated according to the following equations:

$$C = (R_o \sin A_t - Q) \tan A_u + P + R_o \cos A_t$$

$$A_i = \sin^{-1} [C/R) \cos A_u]$$

$$W = C \sin (90° + A_u - A_i)/\sin A_i - (R_o \sin A_t - Q)/\cos A_u$$

$$A_r = \sin^{-1} [(V_s/V_w) \sin A_i]$$

where, as illustrated in FIG. 1, $A_r$ equals the refracted angle in shear mode, $A_i$ equals the incident angle, $A_u$ is the ultrasonic beam angle out of transducer 10, $A_t$ is the transducer 10 rotation angle, Q equals the fixed offset of the transducer 10 from the center of the transducer tilt rotation in a direction parallel or nearly parallel to the beam, P is the fixed offset of transducer 10 from center of the transducer tilt rotation in a direction perpendicular or nearly perpendicular to the beam, R is the bore radius, $R_o$ equals the radial offset of the transducer rotation axis, W is the water path length (the immersion fluid path length), $V_w$ is the velocity of sound in water, and $V_s$ is the shear velocity in steel. The transducer 10 is clamped in a mounting bracket 280 which is part of the transducer carriage 276. The bracket and support arm 278 can be rotated within the carriage 276 which results in transducer rotation $A_t$. The entire carriage 276 is displaced radially to accomplish the second motion $R_o$ required for transducer positioning.

Figure 3:
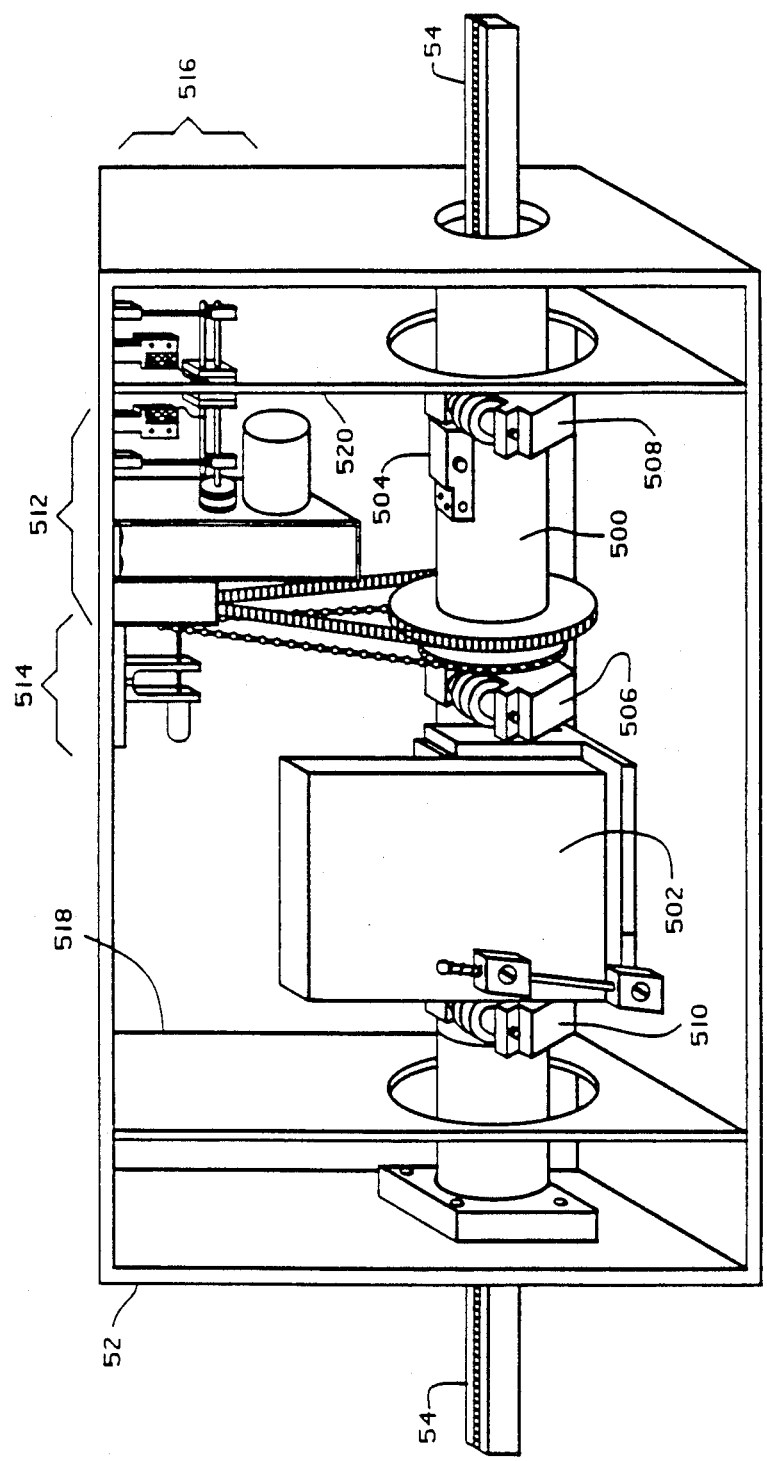
FIG. 3 is a perspective view of a drive box 52.

The basic purpose of the drive box 52 illustrated in FIG. 3 is to transmit axial and circumferential motion through the drive rod 54 to the scan head 46 which holds the ultrasonic transducers 10 that perform the inspection. The drive box 52 includes a carriage tube 500 that runs the length of the drive box 52, an axial drive assembly 502 mounted on the carriage tube 500 which moves the drive rod through box 52. An axial resolver assembly 504, also mounted on the carriage tube 500, indicates the position of the drive rod 54. The drive rod 54 is carried by roller support assemblies 506-510 which are secured to the carriage tube 500 and support the drive rod 54. A circumferential drive assembly 512 rotates the carriage tube 500 and roller assemblies 506-510 in order to rotate drive rod 54. A circumferential resolver assembly 514 is also provided to indicate the circumferential position of the drive rod 54. A limit switch assembly 516 is provided to prevent over rotation of the carriage tube 500 so that drive cables do not get damaged. The drive box 52 also includes cable shields 518 and 520 behind which control cables can be contained and spooled so that the cables do not become entangled with the rotating carriage tube 500 and attached assemblies.

Figure 4:
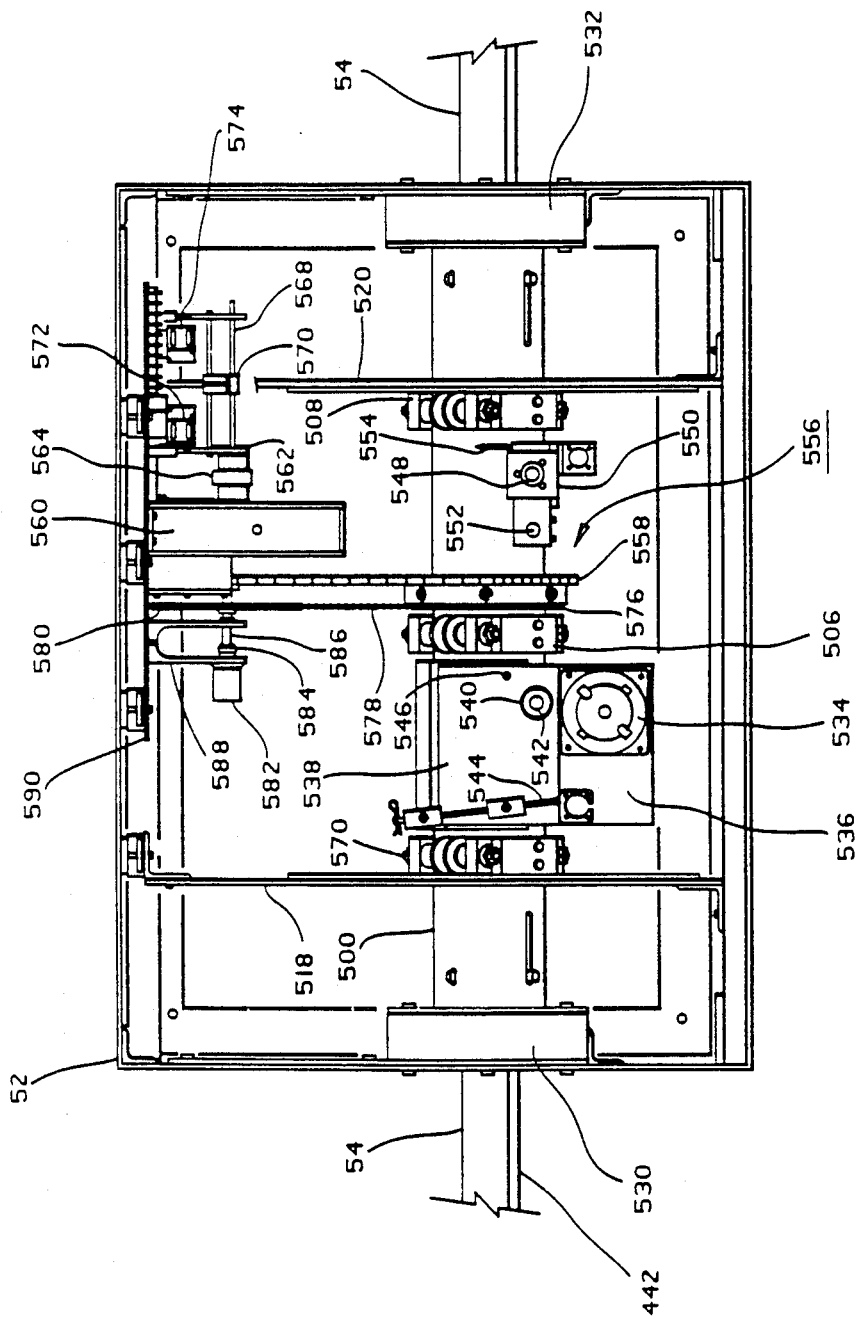
FIG. 4 is a detailed side view of a drive box 52.

The axial drive assembly 502, as illustrated in FIG. 4, includes a motor 534 coupled to a gear reduction box 536 attached to a spring loaded drive mounting box 538. A suitable combination motor-tachometer is available from EG&G Torque Systems of Massachusetts. The axial drive mounting box 538 includes a rack spur gear (not shown) mounted on a spur gear shaft 542 that couples the motion from the motor 34 and gear box 536 to the rack 442 of the drive rod 54. A spring 544 maintains engagement between the rack spur gear and the rack 442 by rotating the axial drive mounting box 538 about pivot 546. The details of the engagement mechanism for the axial drive assembly for the drive rod will be discussed in detail with respect to the details of the resolver engagement mechanism since they are substantially the same.

An axial resolver assembly includes a resolver 548, from one of the suppliers previously mentioned, coupled to a resolver gear (not shown) by a resolver gear shaft mounted in a spring loaded resolver mounting box 550. The mounting box is rotated about pivot 552 and gear contact with the rack 442 is maintained by springs 554 held at one end by a post attached to the carriage tube 500.

As discussed previously, the drive rod is held by roller assemblies 506-510 which are attached to the rotatable carriage tube 500. The carriage tube 500 is rotated by an attached gear 556 driven by a heavy duty steel chain 558. The chain 558 is coupled to a lubricating fluid type circumferential gear box 560 through a chain drive gear (not shown). The gear reduction box 560, which provides a gear reduction ratio of 30 to 1, is driven by a motor 562 which has at least 500 inch-ounces of peak torque that is also available from EG&G Torque systems. The gear box is also coupled to the limit switch assembly 516 which includes a wafer coupling 564 driving a worm gear 568. The worm gear moves a limit switch actuator 570 that engages limit switches 572 and 574. The limit switches immediately disable the drive motor 562 to prevent overrotation of the carriage tube 500 in either direction. The carriage tube 500 is designed to rotate more than 400° and carry sufficient cables for the axial assemblies as it rotates. The control electronics limits the rotation to 400° as discussed earlier and the limit switches prevent overrotation should the electronics fail to stop rotation after 400°.

The circumferential resolver assembly includes a belt drive gear 576 attached to the carriage tube and driving belt 578. A belt drive resolver gear 580 rotates with a one to one ratio with belt gear 576 to rotate resolver 582 through a wafer coupling 584 coupled to the resolver 580 by a shaft 586. The belt 578 and gears 576 and 580 are available from W. M. Berg. The resolver gear 580 and resolver 582 are held in position by a mounting bracket 588 attached to a plate 590.

Figure 5:
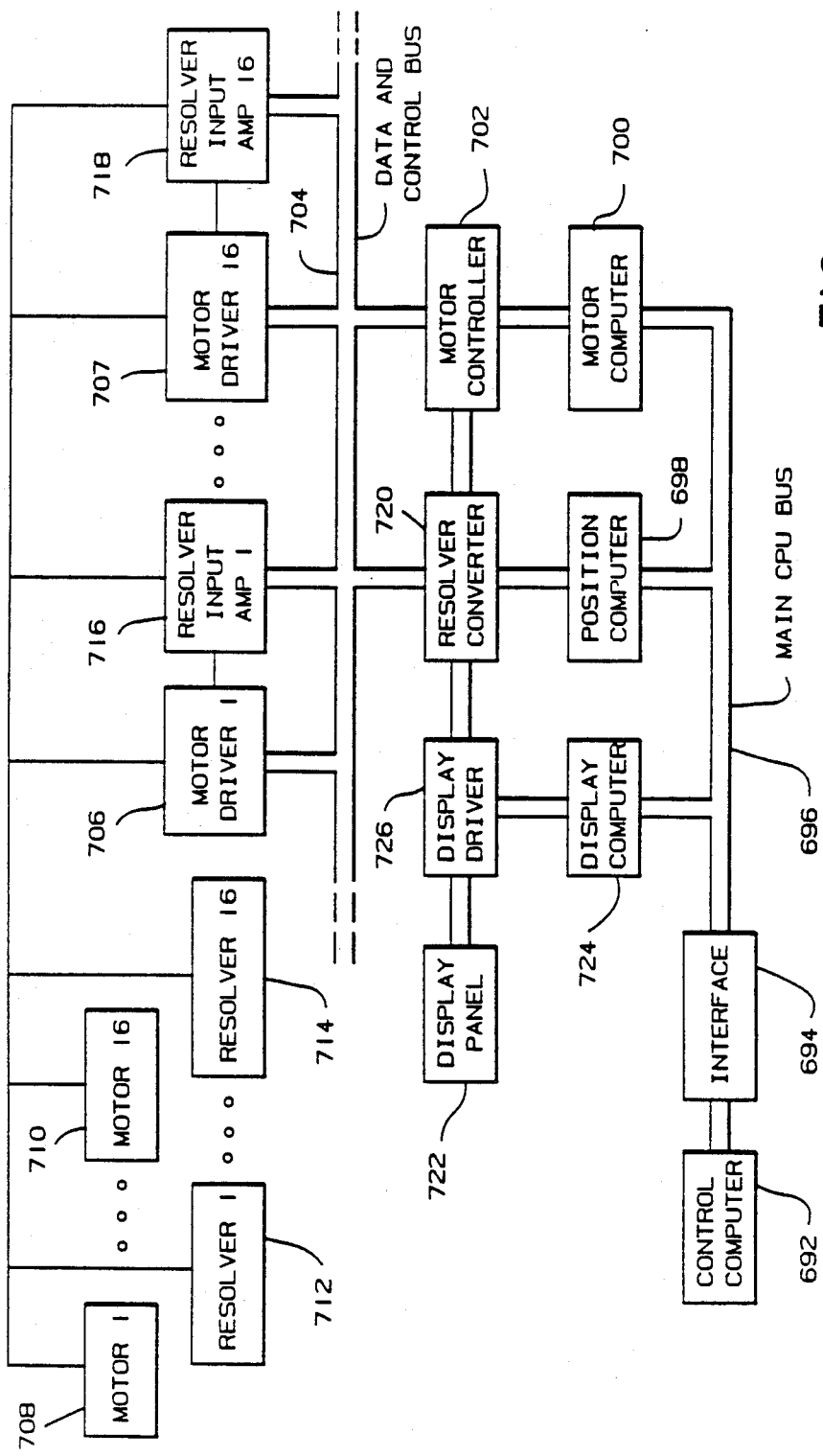
FIG. 5 depicts an electronic control system for controlling motors for various motion axes.

The motors for the 16 scan head motion axes previously discussed are controlled by a computerized control system as illustrated in FIG. 5. In general, a position computer 698 receives a motion command to move one axis of motion from a control computer 692 through interface 694 and over bus 696. The position processor 698 determines the type of motion and issues a command to the motor controller 702 indicating the type of motion and the axis to be moved. The motor processor 700 reads the command and issues a motor speed command including a speed, a direction and a motor driver address to motor controller 702. The motor controller 702 produces a pulse width modulated speed signal which is carried by a data and control bus 704 to all of the motor drivers 706-707. The motor driver having the same address as designated by motor controller 702 accepts the speed signal and direction, and actuates the corresponding one of motors 708-710 over a multiple conductor cable having direct connections between the associated motor driver and motor. A corresponding resolver, as previously discussed, which is mechanically linked to the object being driven by the motor, responds with resolver position signals to the directly connected resolver input amplifiers 716-718 over separate resolver bundles in the multiple bundle cable. The multiple bundle cable includes shielded twisted pairs for resolvers and motors, and micro-miniature coaxial cables for transducer signals. The resolver input amplifier for the corresponding motor driver is actuated by a signal line between the motor driver and the resolver input amplifier to place the resolver signals on a resolver signal portion of data and control bus 704. Note the data and control bus 704 is a separate and different bus than the transducer signal bus discussed in the related application entitled ULTRASONIC SIGNAL PROCESSING SYSTEM INCLUDING A FLAW GATE. The resolver signal, output by the activated resolver input amplifier, is applied to a resolver converter 720 which converts the analog resolver signals into digital values. The motor computer 698 supplies both the position and motor address to a display computer 724. The display computer 724 controls display panel 726 to indicate to the operators the position of the object being controlled.

The computers for the various motion axes provided on the scan head 46 and by the drive box 52 include Z80 processors available from Zilog and appropriate amounts of RAM and PROM memory, and are structured similar to those described in the related application entitled ULTRASONIC SIGNAL PROCESSING SYSTEM INCLUDING A FLAW GATE and will not be discussed in detail here. The motor 700, position 698 and display 724 computers being three such motion axis computers, have a structure identical to the structure illustrated and described in the related application entitled ULTRASONIC SIGNAL PROCESSING SYSTEM INCLUDING A FLAW GATE and will not be discussed in detail here. The registers, latches, etc., discussed hereinafter, are standard off-the-shelf items unless otherwise indicated.

Prior to transducer calibration, operating reference points for the chucks, radial support assemblies, transducer tilt (rotation), axial position and circumferential position must be determined by using reference fixtures and storing the associated positions at which the fixtures are engaged. The offsets between chucks and the various transducers can be determined during calibration using measurement devices to obtain offsets to within 0.01 inches.

As discussed in the related applications identified in the cross references section, the transducers must be calibrated so that reflections located during an inspection scan can be accurately determined as to their location within the rotor being inspected. The calibration starts by mounting the ranging and inspection transducers so that their beams are coincident on the same circumferential location in a calibration block. How a calibration ranging scan is performed during which the ranging offset average times are recorded and the ranging curve is loaded into the flaws, is discussed in more detail in the related application entitled ULTRASONIC SIGNAL PROCESSING SYSTEM INCLUDING A FLAW GATE.

Figure 6:
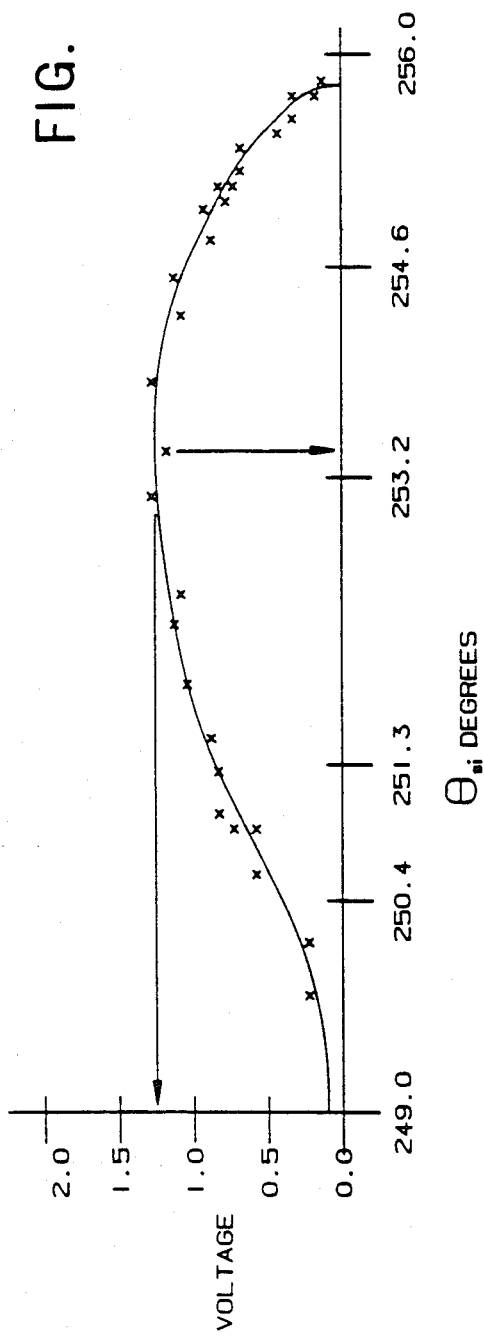
FIGS. 6 and 7 depict curve fitting procedures performed during transducer calibration to calibrate reflector angle and depth.
Figure 7:
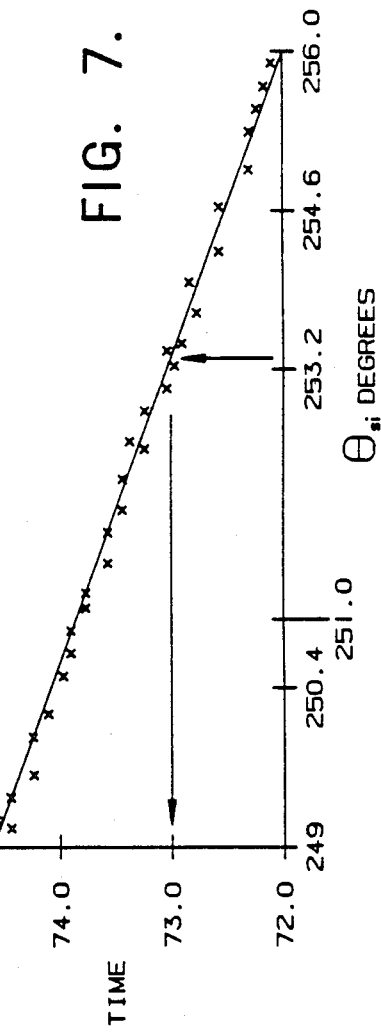

When the ranging scan by the ranging transducer is completed, the inspection transducer is moved into the calibration block and data is recorded from side drilled holes. The data from the known location side drilled holes can be used to manually select the peak signal and enter a circumferential position, time, amplitude and attenuation for the particular side drilled hole. As an alternative, the data can be applied to a curve fitting routine which produces a curve, as illustrated in FIG. 6. The curve can be used to determine the amplitude voltage and the angle at which the peak voltage occurs. The transit times for the reflection from the hole can also be applied to a curve fitting routine to produce a curve, as illustrated in FIG. 7. The angle obtained from the curve of FIG. 6 can be used to determine a measured reflection time using the curve of FIG. 7. The measured angle and measured transit time are then used in the calculations discussed below to determine the operating point of the transducer for the particular hole. From the time and amplitude data for the side drilled holes, the threshold curves, discussed in the related application entitled ULTRASONIC SIGNAL PROCESSING SYSTEM INCLUDING A FLAW GATE, are created for time windows corresponding to the side drilled holes which fall within a particular depth window. It is also possible to use the curve fitting procedure of the present invention with round bottomed holes to adjust not only circumferential position and reflection time but axial offset and tilt using the procedures discussed herein.

During an operating point calibration, suppose we have data from N holes, where N must be no smaller than three. For the $i^{th}$ hole, we have: $d_i$—known hole depth; $\theta_i$—known hole angular position; $t_i$—measured time of peak echo from hole as determined from FIG. 7; $\theta_{si}$—measured circumferential scanner position at the peak echo as determined from FIG. 6. If we define $\Delta\theta_i = \theta_i - \theta_{si}$, then the operating point parameters for a particular window are: $\phi_2$— refracted angle; $t_i$—surface time; $V_2$—metal velocity; and $\theta_{off}$—circumferential offset. The following ray model calculations are then used to determine the operating point parameters:

$$\Delta\theta_i = \theta_{off} + \phi_2 - \left[ \frac{r_b}{r_b + d_i} \sin \phi_2 \right]$$

where $r_b$ equals the radius of the bore;

$$t_i = t_1 + \frac{P_2^i}{V_2}$$

where $P_2^i$ is the path length in the metal from the surface to the hole, and $$P_2^i = \frac{\sin (\phi_2 - B_i)}{\sin \phi_2} (r_b + d_i)$$

where $$B_i = \sin^{-1} \left[ \frac{r_b}{r_b + d_i} \sin \phi_2 \right]$$

The computer then solves for $\theta_{off}$ and $\phi_2$ by minimizing the error $E_i$, $$E_1 = \sum_{i=1}^{N} \left\{ \Delta\theta_i - \theta_{off} - \phi_2 + \sin^{-1} \left[ \frac{r_b}{r_b + d_i} \sin \phi_2 \right] \right\}^2$$

setting $$\frac{\partial E}{\partial \theta_{off}} = \frac{\partial E}{\partial \phi_2} = 0$$

and obtaining $$\sum_{i=1}^{N} \left\{ \Delta\theta_i - \frac{1}{N} \left\{ \sum_{m=1}^{N} \Delta\theta_m + \sum_{m=1}^{N} \sin^{-1} \left[ \frac{r_b}{r_b + d_m} \sin \phi_2 \right] \right\} + \sin \left( \frac{r_b}{r_b + d_i} \sin \phi_2 \right) \right\} \frac{\cos \phi_2}{\left[ \left( \frac{r_b + d_i}{r_b} \right)^2 - \sin^2 \phi_2 \right]^{\frac{1}{2}}} =$$

-continued $$F(\phi_2) = 0$$

This equation is solved for $\phi_2$ using the bisection method. This is a well known method and is discussed in the book "Computer Methods for Mathematical Computations" by Forsythe, Malcolm and Moler. Then, $$\theta_{off} = \frac{1}{N}\left\{\sum_{i=1}^{N} \Delta\theta_i + \sum_{i=1}^{N} \sin^{-1}\left(\frac{r_b}{r_b + d_i}\sin\phi_2\right)\right\} - \phi_2$$

The computer then solves for $t_i$ and $V_2$ by minimizing $E_2$, $$E_2 = \sum_{i=1}^{N}\left(t_i - t_1 - \frac{P_2^i}{V_2}\right)^2$$

$$V_2 = \frac{\sum_{i=1}^{N}(P_2^i)^2 - \frac{1}{N}\left(\sum_{i=1}^{N}P_2^i\right)^2}{\sum_{i=1}^{N}(t_i P_2^i) - \frac{1}{N}\left(\sum_{i=1}^{N}t_i\right)\left(\sum_{i=1}^{N}P_2^i\right)}$$

$$t_1 = \frac{1}{N}\left(\sum_{i=1}^{N}t_i - \frac{1}{V_2}\sum_{i=1}^{N}P_2^i\right)$$

If the operating point is determined, and it is not as desired by the operator, the transducer mounting can be adjusted and the procedure repeated to obtain the desired operating point for the channel/window of interest. The times $t_i$ and amplitudes of the reflections for each hole within each window are used to create threshold curves used to determine whether a signal contains reportable indications. The threshold procedure is discussed in more detail in the related application entitled ULTRASONIC SIGNAL PROCESSING SYSTEM INCLUDING A FLAW GATE and is not discussed further herein.

After the operating point calibration procedure discussed above is performed, the scan head is moved into a rotor bore to perform an inspection. At the beginning of each scan for each axial position, a ranging scan is performed using the ranging transducer in which adjusted delays for the surface time are determined and loaded as curves into the flaw gates discussed in detail in the related application entitled ULTRASONIC SIGNAL PROCESSING SYSTEM INCLUDING A FLAW GATE. The preferred high speed scan method produces separate pulses focused in the center of each depth/time window that are rapidly generated to provide complete coverage of the first four to six inches of the rotor during high speed circumferential motion. The flaw gates then record hit data which include a range corrected reflection time, a scanner angle and the amplitude. The control computer 692 then retrieves the data from the flaw gates and performs the calculations below necessary to pinpoint the depth, angle and axial position of each flaw indication.

The time in microseconds, for each reflection is calculated from an integer waveform index provided by the flaw gate, $$T_{raw} = 0.05 \text{ (index)} + \text{delay}$$

where 0.05 is the sampling interval in microseconds, and the delay equals the transit time delay of the flaw gate. The waveform index is corrected by a ranging offset in the flaw gate, as discussed in the related application. Next the time T and circumferential position C are converted to depth D and angle according to the following calculations:

$$P_2 = \frac{1}{2}V_2(T - t_1)$$

where $P_2$ equals the path length in the metal; $V_2$ equals the sound velocity in the metal; and $t_1$ is the surface time; that is, the time for the inspection pulse to reach the bore surface 26 and return; and then, $$D = \sqrt{P_2^2 + r_b^2 + 2P_2 r_b \cos\phi_2} - r_b$$

where $\phi_2$ is refracted angle and $r_b$ is the bore radius $$\theta = C + \theta_{off} + \phi_2 - \sin^{-1}\left[\frac{r_b}{r_b + D}\sin\phi_2\right]$$

Recall that $V_2$, $t_1$, $\phi_2$ and $\theta_{off}$ are the constants determined during calibration. True axial position Z is then calculated from scanner axial position APOS $$Z = APOS - AXOFF$$

where AXOFF is the transducer mounting offset. If round bottom holes were used during calibration to determine any tilt of the beam, the true axial position is adjusted using $$Z = APOS - AXOFF + \alpha D$$

where $\alpha$ equals slope and D equals depth.

Figure 9:
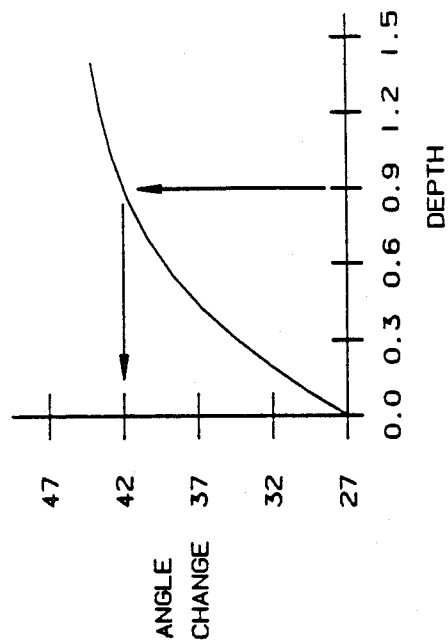
FIGS. 8 and 9 illustrate a procedure for locating the position and depth of flaws during an inspection.
Figure 8:
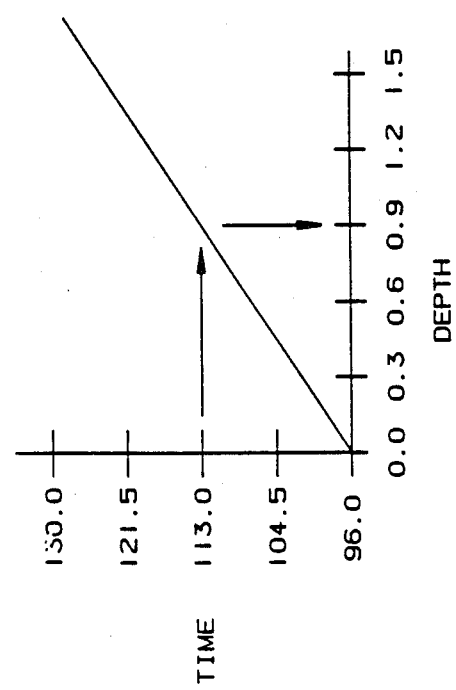

In the alternative to the calculations discussed above, it is possible to use table lookup methods to determine the depth from the reflection time using a curve, as illustrated in FIG. 8, stored in a time to depth conversion table. The depth is then used to produce an angle change from a depth to angle change conversion table which represents a curve, as illustrated in FIG. 9. Once the depth, angle of the flaw and true axial position are determined, a known graphic display program can be used to provide an image of the indication in several different views such that the size and location of the flaws within the rotor can be determined. Rotor life time predictions can then be made based on size and location of flaws.

Descriptions of additional components of the present invention can be found in U.S. Pat. No. 4,757,716.

The many features and advantages of the invention are apparent from the detailed specification and thus it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described and accordingly, all suitable modifications and equivalents may be resorted to, falling within the scope of the invention.

What is claimed is:

1. A location method for locating unknown location ultrasonic reflections in a radial-circumferential plane in a rotor using a transducer in a bore of the rotor, comprising the steps of:
  (a) recording calibration transit times of an ultrasonic wave reflected from holes located at know hole radial and circumferential positions in a calibration block having an inner diameter, where at least three holes are at different radial positions;
  (b) recording transducer circumferential positions of the transducer corresponding to the calibration transit times;
  (c) determining a refracted angle of the ultrasonic wave inside the calibration block from the transducer circumferential positions along with the known hole radial and circumferential positions;
  (d) computing a circumferential offset from the refracted angle and the known hole radial and circumferential positions;
  (e) determining a velocity of the ultrasonic wave inside the calibration block from the calibration transit times, the refracted angle, and the know hole radial positions;
  (f) computing a surface transit time, which is a time for the ultrasonic wave to travel from the transducer to the bore surface and back to the transducer, from the velocity, the calibration transit times and the known hole radial positions;
  (g) recording a reflector transit time and a reflector circumferential position for a reflector at an unknown location in the rotor having the same diameter as the calibration block; and
  (h) calculating reflector radial and circumferential positions of the reflector from the reflector transit time and circumferential positions using the refracted angle, the circumferential offset, the velocity and the surface transit time.

2. A method as recited in claim 1, wherein step (c) comprises using a least squares procedure for minimizing an error between a measured circumferential position determined in step (b) and a known circumferential position determined in step (a).

3. A method as recited in claim 1, wherein step (e) comprises using a least squares procedure minimizing an error between a recorded transit time determined in step (a) and a know transit time determined in step (a).

4. A method as recited in claim 1, wherein the holes are round bottomed holes.

5. A method as recited in claim 1, wherein the holes are side drilled holes.

6. A location method for locating unknown location ultrasonic reflectors in three dimensions in a rotor using a transducer in a bore of the rotor, comprising the steps of:
  (a) recording calibration transit times of an ultrasonic wave reflected from holes located at known axial, radial and circumferential positions in a calibration block having a diameter, where at least three of the holes are at different radial positions;
  (b) recording circumferential and axial positions of the transducer corresponding to the calibration transit times;
  (c) determining a refracted angle in the radial-circumferential plane of the ultrasonic wave inside the calibration block from the recorded circumferential positions along with the known hole radial and circumferential positions;
  (d) computing a circumferential offset from the refracted angle and the known hole radial and circumferential positions;
  (e) determining a velocity in the radial-circumferential plane of the ultrasonic wave inside the calibration block from the calibration transit times, the refracted angle, and the known hole radial positions;
  (f) computing a surface transit time, which is a time for the ultrasonic wave to travel from the transducer to the bore surface and back to the transducer, from the velocity, the calibration transit times and known hole radial positions;
  (g) determining an axial position of an entry point of the ultrasonic wave into the calibration block and an axial tilt of the ultrasonic wave in the calibration block as a function of radial position from the recorded axial positions and the know hole radial positions;
  (h) recording a reflector transit time, axial position and circumferential position for a reflector at the unknown location in the rotor having the same diameter as the calibration block; and
  (i) calculating reflector radial, axial and circumferential positions of the unknown reflector from the reflector transit time, axial position and circumferential position using the refracted angle, the circumferential offset, the velocity, the surface transit time, the entry point axial position and the axial tilt.

7. A method as recited in claim 6, wherein step (c) comprises using a least squares procedure for minimizing an error between recorded circumferential position determined in step (b) and known circumferential position determined in step (a).

8. A method as recited in claim 6, wherein step (e) comprises using a least squares procedure minimizing an error between a known transit time determined in step (a) and a recorded transit time determined in step (a).

9. A method as recited in claim 1 wherein the holes are round bottomed holes.

10. A method as recited in claim 6, wherein the holes are side drilled holes.

* * * * *